US010201662B2

(12) United States Patent
Morris et al.

(10) Patent No.: US 10,201,662 B2
(45) Date of Patent: Feb. 12, 2019

(54) INJECTION DEVICE AND ASSEMBLY METHOD

(71) Applicant: Sanofi, Paris (FR)

(72) Inventors: Anthony Paul Morris, Coventry (GB); William Marsh, Buckingham (GB); Matthew Jones, Warwick (GB); Joseph Butler, Rugby (GB); David Aubrey Plumptre, Droitwich Spa (GB); Robert Veasey, Leamington Spa (GB)

(73) Assignee: Sanofi, Paris (FR)

( * ) Notice: Subject to any disclaimer, the term of this patent is extended or adjusted under 35 U.S.C. 154(b) by 297 days.

(21) Appl. No.: 14/782,667

(22) PCT Filed: Apr. 8, 2014

(86) PCT No.: PCT/EP2014/056967
  § 371 (c)(1),
  (2) Date: Oct. 6, 2015

(87) PCT Pub. No.: WO2014/166889
  PCT Pub. Date: Oct. 16, 2014

(65) Prior Publication Data
  US 2016/0045672 A1  Feb. 18, 2016

(30) Foreign Application Priority Data

Apr. 10, 2013 (EP) .................................. 13163065

(51) Int. Cl.
  *A61M 5/00* (2006.01)
  *A61M 5/315* (2006.01)
  *A61M 5/31* (2006.01)
(52) U.S. Cl.
  CPC ...... *A61M 5/31533* (2013.01); *A61M 5/3146* (2013.01); *A61M 5/31541* (2013.01); *A61M 2207/00* (2013.01)

(58) Field of Classification Search
  CPC ........ A61M 2005/2407; A61M 5/3146; A61M 5/31585; A61M 5/24; A61M 2205/581;
  (Continued)

(56) References Cited

U.S. PATENT DOCUMENTS 9,707,352 B2 * 7/2017 Helmer ............. A61M 5/31536
9,867,614 B2 * 1/2018 Williams ........... A61B 17/1155
  (Continued)

FOREIGN PATENT DOCUMENTS

CN   102238973   11/2011
EP   2 201 972   6/2010
  (Continued)

OTHER PUBLICATIONS

International Preliminary Report on Patentability in International Application No. PCT/EP2014/056967, dated Oct. 13, 2015, 6 pages.
  (Continued)

*Primary Examiner* — Phillip Gray
(74) *Attorney, Agent, or Firm* — Fish & Richardson P.C.

(57) ABSTRACT

An injection device includes a housing containing a cartridge containing a medicament and a movable bung. The housing includes an inner thread. The injection device includes a piston rod for moving the bung during dose dispensing. The piston rod includes an outer thread engaging the inner thread of the housing a bearing at its end facing the bung. The injection device further includes a driver coupled to the piston rod for driving the piston rod during dose dispensing. In the unused delivery state of the device, the bearing abuts the bung. The invention further refers to an assembly method for such an injection device.

19 Claims, 4 Drawing Sheets

(58) Field of Classification Search
CPC ........ A61M 2205/582; A61M 5/31543; A61M 5/31501; A61M 3/3156; A61M 2205/583; A61M 5/14566; A61M 5/31541; A61M 5/31575; A61M 5/31555; A61M 2005/3126
USPC ......... 604/131–155, 207, 208, 211, 224, 228
See application file for complete search history.

(56) References Cited

U.S. PATENT DOCUMENTS

| | | | | |
|---|---|---|---|---|
| 2003/0160072 | A1* | 8/2003 | Geiser | A61M 5/24 222/327 |
| 2004/0000818 | A1* | 1/2004 | Preuthun | A61M 5/14566 310/83 |
| 2008/0287883 | A1* | 11/2008 | Radmer | A61M 5/31545 604/211 |
| 2010/0137791 | A1* | 6/2010 | Plumptre | A61M 5/3146 604/68 |
| 2012/0041387 | A1* | 2/2012 | Bruggemann | A61M 5/14546 604/218 |
| 2012/0172804 | A1* | 7/2012 | Plumptre | A61M 5/14244 604/154 |
| 2012/0283659 | A1* | 11/2012 | Kouyoumjian | A61M 5/31551 604/211 |
| 2013/0218130 | A1* | 8/2013 | Plumptre | A61M 5/24 604/506 |
| 2015/0209522 | A1* | 7/2015 | Jugl | A61M 5/31515 604/228 |

FOREIGN PATENT DOCUMENTS

| | | |
|---|---|---|
| JP | 2001-502196 | 2/2001 |
| JP | 2012-512673 | 6/2012 |
| JP | 2013-506446 | 2/2013 |
| TW | 317503 | 10/1997 |
| TW | 426531 | 3/2001 |
| TW | 326838 | 2/2008 |
| WO | WO 97/21457 | 6/1997 |
| WO | WO 98/10814 | 3/1998 |
| WO | WO 99/48546 | 9/1999 |
| WO | WO 2004/078241 | 9/2004 |
| WO | WO 2010/063704 | 6/2010 |
| WO | WO 2011/039207 | 4/2011 |
| WO | WO 2011/039229 | 4/2011 |
| WO | WO 2011/068531 | 6/2011 |

OTHER PUBLICATIONS

International Search Report and Written Opinion in International Application No. PCT/EP2014/056967, dated Jun. 25, 2014, 9 pages.

* cited by examiner

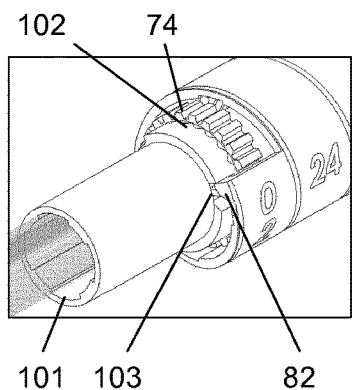
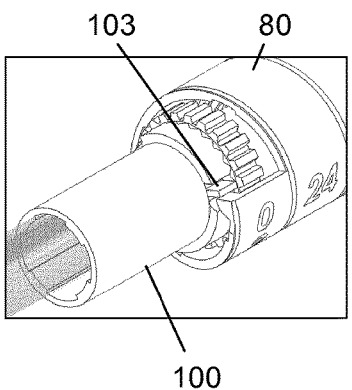
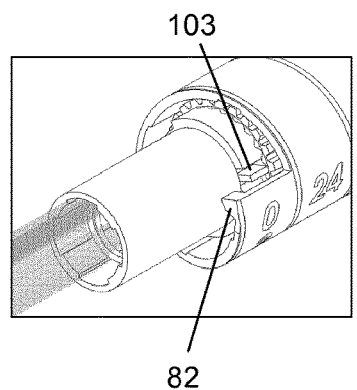
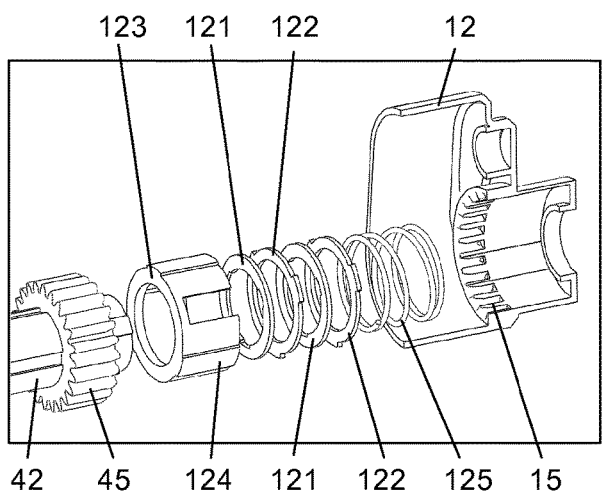
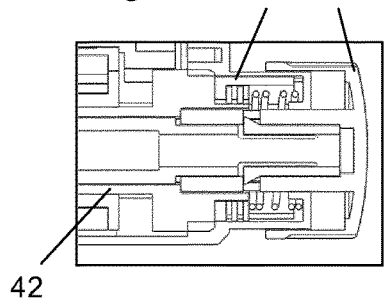
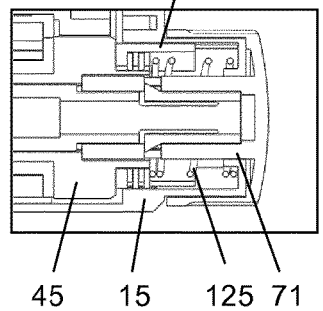
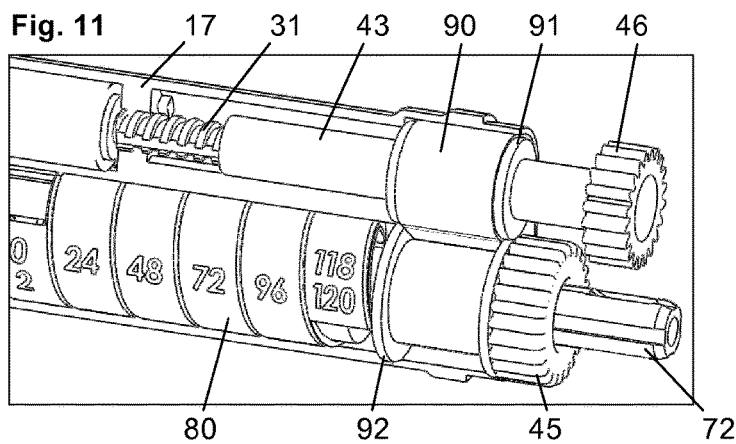

INJECTION DEVICE AND ASSEMBLY METHOD

CROSS-REFERENCE TO RELATED APPLICATIONS

This application is a U.S. national stage application under 35 USC § 371 of International Application No. PCT/EP2014/056967, filed on Apr. 8, 2014, which claims priority to European Patent Application No. 13163065.9, filed on Apr. 10, 2013, the entire contents of which are incorporated herein by reference.

The present invention is generally directed to a handheld injection device, i.e. a drug delivery device for selecting and dispensing a number of user variable doses of a medicament.

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present invention is in general applicable for both types of devices, i.e. for disposable devices as well as for reusable devices.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices can involve springs which are (partly) preloaded and springs which are mainly loaded by the user during dose selecting. Some stored-energy devices use a combination of spring preload and additional energy provided by the user, for example during dose setting. In general, the present invention is applicable for all of these types of devices, i.e. for devices with or without a drive spring.

These types of pen delivery devices (so named because they often resemble an enlarged fountain pen) are generally comprised of three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A disposable drug delivery device for selecting and dispensing a number of user variable doses of a medicament according to the present invention typically comprises a housing, a cartridge holder for receiving a cartridge, a lead screw or piston rod and means for driving the piston rod during dose dispensing. Such a disposable drug delivery device is known from WO 2004/078241 A1, wherein the cartridge holder is rigidly attached to the device housing. The piston rod, which acts on a cartridge bung, is advanced by a driver during dose dispensing. This known device is a manually driven device, where the component parts are in general disposed concentrically around a common longitudinal axis. During dose setting some component parts wind out of the housing and are pushed back into the housing during dose dispensing.

Usually, injection devices require a so called priming prior to the first use to close a possible gap between the cartridge bung and the piston rod and to overcome tolerances within the device. For the priming step, a user has to set a small dose and to dispense this dose while monitoring whether e.g. fluid leaves the device. This action has to be repeated until e.g. fluid actually leaves the device. There is a risk of an underdosage at least during the first use of the device if a user does not perform this priming step.

In US 2010/0137791 A1 the term "priming of the device" is used with a different meaning, namely for removing gaseous inclusions in the fluid, like air bubbles. Removing such gas is done by expelling a small dose of the fluid from the device while pointing the device for example needle-up. As medication is usually rather expensive, expelling medication should be kept at a minimum.

It is an object of the present invention to provide an improved drug delivery device and an assembly method for such a device eliminating this risk. It is a further object to improve user friendliness and handling and to make the drug delivery device compact in size, preferably without components translating out of the housing during dose setting.

This object is solved by a device as defined in claim 1.

According to a first embodiment of the present invention the injection device comprises a housing containing a cartridge, which may contain a medicament, and a movable bung. The housing comprises an inner thread. The device further comprises a piston rod (lead screw) for moving the bung during dose dispensing, with the piston rod comprising a bearing at its end facing the bung and an outer thread, which engages the inner thread of the housing. Further, a driver is provided coupled to the piston rod for driving the piston rod during dose dispensing. To avoid the requirement of a priming step, the bearing abuts the bung in the unused delivery state of the device. It is also desirable to apply a small force to the bung at least when the dispense button of the device is pressed. In other words, priming is no longer necessary because when the device is given to a user for the first use, the bung and the bearing are already in contact with each other. According to the invention, the unused delivery state of the device shall mean the state of the device as it is sold and delivered to customers. Typically, this is the state in which a user takes the device out of its packaging. Thus, the device is ready to use, which eliminates the requirement of a priming step prior to the first use.

This prime elimination may be achieved in a device where the driver is coupled to the piston rod by rotating the driver during the assembly process until the piston rod is moved to a position abutting the cartridge bung. This position may be determined by an increase in the force or torque required to rotate the driver. As an alternative, the axial position of the piston rod relative to the housing may be sensed. According to a further alternative, the piston rod may be pushed towards the bung or the cartridge may be pushed towards the piston rod to close a potential gap between the piston rod bearing and the cartridge bung.

The object of the present invention is further solved by a method as defined in claim 18 and a device assembled or manufactured as defined in claim 18. The assembly method comprises the steps of positioning a cartridge, a piston rod and a drive tube in a housing, preferably with the drive tube being in splined or threaded engagement with the piston rod, thereafter rotating the drive tube and the piston rod relative to the housing in a direction moving the piston rod towards a cartridge bung until the piston rod or a bearing thereof abuts the bung. This has the effect, that any potential gap between the bung and the piston rod or its bearing as well as potential tolerances between the cartridge bung, the piston rod and/or the drive tube are eliminated such that the device is ready to use without requiring a priming step. Preferably, the drive tube is rotationally coupled to a drive sleeve after this gap elimination. For example, the drive tube and the drive sleeve may be rotationally coupled to each other, e.g. by meshed gear engagement, such that rotation of the drive sleeve in a first direction causes rotation of the drive tube in a second, opposite direction.

A further aspect of the present invention is the sensing of the point at which the piston rod touches the bung. This is achieved by using its position relative to the housing. In more detail, the piston rod is in threaded engagement with the housing, which always includes at least a small axial play between the piston rod and the housing, i.e. the thread form of the piston rod may contact either the distal side or the proximal side of the corresponding thread form of the housing. During insertion of the piston rod, this contact may be on the distal side, whereas the abutment of the bung and the piston rod shifts the piston rod back within the thread form such that the thread form of the piston rod contacts the proximal side of the corresponding thread form of the housing. The point at which the piston rod moves to the opposite sides of its threaded engagement with the housing thus indicates contact with the bung.

This method of prime elimination can be applied to devices of many different formats. In the following, advantageous features and preferred embodiments of an injection device according to claim 1 or an injection device assembled according to claim 18 are listed which may be provided in the devices independent of each other:

Preferably, the injection device has a driver comprising a drive tube and a drive sleeve, which may be arranged on different, parallel longitudinal axes. In this case, the step of rotating the drive tube and the piston rod relative to the housing is performed with the drive tube being rotationally decoupled from the drive sleeve. Further, after the piston rod or its bearing abuts the bung, the drive tube is rotationally coupled to the drive sleeve.

According to a further embodiment the injection device comprises a housing, a piston rod, a driver, a dose setting means, and optionally a power reservoir and/or a release clutch. The piston rod preferably defines a first longitudinal axis and is located within the housing. The driver is coupled to the piston rod. The dose setting means is rotatable about a second longitudinal axis at least during dose setting. The optional power reservoir may be provided for driving the driver during dose dispensing. Preferably, the release clutch is arranged such that it prevents rotation of the driver during dose setting and allows rotation of the driver during dose dispensing. The first longitudinal axis is spaced from the second longitudinal axis, i.e. there is an offset between the two axes on which the component parts of the device are arranged. Preferably, the first longitudinal axis is parallel to the second longitudinal axis. As an alternative, the two axes may be tapered, but still with an offset between the axes within the device. Due to some of the component parts being located next to others instead of the conventional concentrically arrangement, the cross-section of the device becomes rather elongated than the usual circular pen-shape. This improves handling of the device at least for some users. Further, the device may be made shorter, which again improves handling and convenience. Providing the power reservoir for driving the driver reduces the force required for the user during dose dispensing. This is especially helpful for users with impaired dexterity.

The power reservoir may comprise a spring, which may be a preloaded (pre-charged) spring or a spring which has to be loaded by the user during dose setting, for example a torsion spring. Preferably, the spring is fully pre-charged for the expected life of the device, (reducing the effort required to use the device) i.e. such that a user is not required to re-charge or strain the spring at any time. Suitable spring types include compression springs and torsion springs. According to a preferred embodiment of the invention, the spring is a reverse wound flat spiral spring, which is a wound up band-type spring which is wound up in its charged state counter to its unstressed winding direction. Preferably, a first end of the spring is attached to a first spool, which may be located on the first longitudinal axis, and a second end of the spring is attached to a second spool, which may be located on the second longitudinal axis. For driving the driver, one of the spools may be coupled to the driver, e.g. by means of a direct splined coupling. As an alternative, a releasable coupling may be used, e.g. a pair of teeth rings.

The driver may comprise a tubular element which is coupled to the piston rod. Preferably, this tubular element at least partly surrounds the piston rod. The coupling may be a releasable coupling, however it is preferred that the driver is permanently coupled to the piston rod, e.g. via a splined interface or a threaded interface. A drive tube being a component part of the driver is preferably arranged rotatably about the first longitudinal axis and directly coupled to the piston rod.

The driver may further comprise at least one further component part, for example a drive sleeve which is rotatable about the second longitudinal axis. Thus, two component parts of the driver may be arranged with an offset on parallel axes. Preferably, the component parts of the driver are permanently coupled to each other in the unused delivery state of the device such that rotation of one component causes rotation of the other component. For example meshing gears might be provided on each of the two driver components. Preferably, the component parts of the driver are coupled to each other such that the drive tube and the drive sleeve rotate in opposite directions. The drive sleeve may be coupled to the power reservoir such that the power reservoir drives the driver components, e.g. via a splined interface. For manufacturing or assembly reasons, the drive sleeve may comprise two or more component parts, which are rigidly connected to each other during assembly such that they act in the device as one component.

According to a further preferred embodiment, the dose setting means comprises a dial assembly and a dial sleeve which are rotatable about the second longitudinal axis. Preferably, the dial assembly is decoupled from the driver during dose setting and, for example a part of the dial assembly like a number sleeve or dose indicator, is coupled to the driver during dose dispensing. However, according to an embodiment of the invention, further parts of the dial assembly, like a dial part, should not be coupled to the drive during dose dispensing. The dial assembly may comprise a dial grip extending at least partially from the housing, which allows a user to select or deselect a dose by rotating the dial grip. The dial grip may further be used as a trigger or release button to initiate dose dispensing. The dial assembly may further comprise a sleeve-like part for interaction with further components. For manufacturing or assembly reasons, the dial grip and the sleeve-like part may comprise two or more component parts, which are rigidly connected to each other during assembly such that they act in the device as one component. Preferably, the dial sleeve may be rotationally coupled and de-coupled with the dial assembly. For example, it is preferred, if rotation of the dial grip is transferred to the dial sleeve during dose setting and/or dose correction, whereas during dose dispensing rotation of the dial sleeve does not entrain the dial grip.

Injection devices usually have a display indicating the current set dose. This might include mechanical displays and electronic displays. Preferably, the device further comprises a number sleeve having a series of numbers and/or symbols on its outside. Typically, a window in the housing allows only the number or symbol corresponding to the current set dose to be viewed from the outside of the device. If the number sleeve is in threaded engagement with the housing and is splined to the dose setting means, the number sleeve may rotate together with the dial sleeve during dose setting (and dose correction) and during dose dispensing. Due to the threaded interface with the housing, the number sleeve travels axially within the housing upon rotation of the number sleeve. Preferably, the number sleeve is rotatable about the second longitudinal axis.

If the piston rod is a threaded lead screw with the housing having a threaded portion cooperating with a threaded outer surface of the piston rod, rotation of the piston rod during dose dispensing results in an axial movement of the piston rod. As an alternative the piston rod may be in threaded engagement with the driver and be splined to the housing.

According to a preferred embodiment, the drug delivery device comprises a limiter mechanism defining a maximum settable dose and a minimum settable dose. Typically, the minimum settable dose is zero (0 IU of insulin formulation), such that the limiter stops the device at the end of dose dispensing. The maximum settable dose, for example 60, 80 or 120 IU of insulin formulation, may be limited to avoid overdosage. Preferably, the limits for the minimum dose and the maximum dose are provided by hard stop features.

The limiter mechanism may comprise a first rotational stop on the number sleeve and a first counter stop on the housing, which abut in the minimum dose (zero) position, and a second rotational stop on the number sleeve and a second counter stop on the housing, which abut in the maximum dose position. As the number sleeve rotates relative to the housing during dose setting and during dose dispensing, these two components are suitable to form a reliable and robust limiter mechanism.

To prevent an underdosage or a malfunction, the drug delivery device may comprise a last dose protection mechanism for preventing the setting of a dose, which exceeds the amount of liquid left in a cartridge. For example, the last dose protection mechanism comprises a nut member located interposed between the driver (or any other component that rotates only during dose dispense) and the dial sleeve or any other component which rotates during dose setting and dose dispensing. In a preferred embodiment, the dial sleeve rotates during dose setting and during dose dispensing, whereas the driver only rotates during dose dispensing together with the dial sleeve. Thus, in this embodiment, the nut member will only move during dose setting and will remain stationary with respect to these components during dose dispensing. Preferably, the nut member is threaded to the dial sleeve and splined to the driver. As an alternative, the nut member may be threaded to the driver and may be splined to the dial sleeve. The nut member may be a full nut or a part thereof, e.g. a half nut.

Initiating dose dispensing usually requires that a user presses a button or trigger. Preferably, at least one component part of the dose setting means and/or the driver is axially displaceable between a dose setting position, in which the dose setting means is rotatable relative to the housing and relative to the driver, and a dose dispensing position, in which the driver is rotatable relative to the housing. The axially displaceable dose setting means may be a dial grip which is used for dose setting. Preferably, the axially displaceable component travels along the second longitudinal axis between its dose setting position and its dose dispensing position.

The sequence of dose setting and dose dispensing usually requires a relative movement of some of the components either during dose setting and/or during dose dispensing. Various different embodiments of achieving this result are possible, some of which are described in the prior art mentioned above. According to a preferred example of the invention, the injection device may further comprise a clutch arranged between the drive member and the number sleeve, wherein the clutch allows relative rotation of the drive member and the number sleeve during dose setting and rotationally constrains the drive member and the number sleeve during dose dispensing. This embodiment may include a relative axial movement during dose setting.

According to a further embodiment of the present invention the handheld injection device comprises a housing, which may contain a cartridge, a dose setting means, which is operable, e.g. rotatable, in a first direction to set a desired dose to be dispensed, a piston rod, which is adapted to cooperate with a piston or bung so as to cause a set dose to be injected from the cartridge, and first and second clicker components. The first clicker component may be rotationally constrained to the housing, whereas the second clicker component may be rotatable relative to the housing during dose dispensing. To provide a non-visual, i.e. an audible and/or tactile, first feedback to a user only close to the end of dispensing of a set dose, the clicker components are adapted to contact each other. If the first clicker component is axially displaceable relative to the housing between a proximal dose setting position and a distal dose dispensing position, the first feedback is generated only if the device is in its dose dispensing mode with the first clicker component being in its distal dose dispensing position. However, if the device is in its dose setting mode with the first clicker component being in its proximal dose setting position, the two clicker components do not engage with each other, thus preventing that a signal or feedback is generated. Thus, dialing up from a minimum dose of zero, will not require any resetting step of the clicker arrangement because no contact occurs between the clicker components.

A further advantage of the first clicker component being axially displaceable relative to the housing between a proximal dose setting position and a distal dose dispensing position, is that the dose setting means may be operable, e.g. rotatable, in a second direction which is opposite to the first direction to cancel a set dose, without the first and second clicker components contacting each other and, thus, without creating the 'end of dose' feedback. This avoids confusion of the users.

Preferably, the injection device further comprises at least one clicker producing an audible and/or tactile feedback during dose setting and/or during dose correction (cancelling of a set dose without dispensing) and/or during dose dispensing. To differentiate between these feedback signals, the first feedback (end of dose dispensing feedback), which is generated only at the end of dispensing of a set dose, is distinct from the further feedback(s). For example, a different sound may be generated.

According to an embodiment of the invention, the second clicker component is a number sleeve, e.g. a tubular element having numbers, symbols or the like on its outer surface, which are visible from the outside of the device, e.g. through a window or aperture in the housing. The number sleeve is preferably in threaded engagement with the housing and splined to the dose setting means.

There are various suitable ways of generating the non-visual, i.e. an audible and/or tactile, feedback signal(s), like a change in a rotational velocity of at least one part, e.g. by changing the pitch of a threaded portion or by engaging a non-rotating part and a rotating part, thereby causing the non-rotating part to start rotating. The feedback may alternatively be generated by building up and releasing a tension. Preferably, the first clicker component has a radially inwards directed protrusion, for example a ramp, and the second clicker component has a flexible element, like a spring arm or finger, which extends radially outwards from the second clicker component. Due to the second clicker component being axially movable, the second clicker component can be positioned such that during dose dispensing the protrusion of the first clicker component contacts the flexible element of the second clicker component. For example, the ramp may flex the spring arm, which snaps back to its unstressed position after disengagement with the ramp, which generates the feedback signal.

To improve handling of the device, the length of the device before and after dose setting is preferably the same. In other words, there is no dial extension due to components winding out of the housing during dose setting. Preferably, the dose setting means and the driver are arranged in the housing such that they are prevented from axial displacement along one of the longitudinal axes during dose setting and during dose dispensing. However, an axial movement of at least some of the components between dose setting and dose dispensing may be possible for switching between a dose setting position and a dose dispensing position of the device.

According to a preferred embodiment, the dose setting means comprises a release button which is axially displaceable along the second longitudinal axis, wherein the device further comprises friction means for decelerating the driver depending on the position of the release button. In other words, a speed control is provided which allows the user to vary the dispensing speed of the device. The friction means may comprise one or more clutch plates or other component parts of the device which are pressed against each other, e.g. by a spring. One of these plates or components rotates during dose dispensing whereas a further of these plates or components is held stationary during dose dispensing. Thus friction is caused by the relative movement of these components which decelerates the device. Pressing the release button decreases the friction, e.g. by lowering the spring force, which thus, leads to an increase of the dispensing speed. Preferably, the release button is the dial grip of the dose setting means.

The cartridge of the drug delivery device may contain a medicament.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antihousing or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp- Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antihousing is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antihousing; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antihousing contains two light chains that are always identical; only one type of light chain, κ or λ, is present per antihousing in mammals.

Although the general structure of all antibodies is very similar, the unique property of a given antihousing is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antihousing fragment" contains at least one antigen binding fragment as defined above, and exhibits essentially the same function and specificity as the complete antihousing of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The present invention provides a mechanism for use in a medical device that can be operated to deliver a number of user variable doses of medicament from a cartridge, via a needle. The device is disposable and is delivered to the user in a fully assembled condition ready for use.

The mechanism uses a motor spring to store energy. This is supplied to the user in a pre-charged state and no subsequent recharging is necessary for the entire life of the device. The user selects the required dose using an input dial and set dose display incorporated into the mechanism. The spring energy is stored until the device is triggered for dispense at which point a proportion of the energy stored is used to deliver the medicament from the cartridge to the user.

Any dose size can be selected between zero and a predefined maximum, in one unit increments. The mechanism permits cancelling of a dose without any medicament being dispensed, by rotation of the dose selection dial (dial grip) in the opposing direction to when selecting a dose.

The trigger is positioned towards the proximal end of the device and, on activation, dispenses medicament if the dose selected is greater than zero.

The device has low torque requirements to set a dose since the spring is pre-charged and low force requirements to trigger dispense of medicament. It has relatively low part count and is particularly attractive for cost sensitive device applications.

The mechanism has the added advantage that several key components are arranged in parallel driven by a gear arrangement. This reduces the overall length of the device.

Non-limiting, exemplary embodiments of the invention will now be described with reference to the accompanying drawings, in which:

FIG. 8a shows an enlarged view of a detail of the device of FIG. 1 in the dose dispensing state;

FIG. 8b shows an enlarged view of a detail of the device of FIG. 1 in the dose dispensing state;

FIG. 8c shows an enlarged view of a detail of the device of FIG. 1 in the dose setting state;

FIG. 9 shows an exploded view of components of an injection device in accordance with a second embodiment of the present invention;

FIG. 10a shows a view of a detail of the device of FIG. 9 in the dose setting state;

FIG. 10b shows a view of a detail of the device of FIG. 9 in the dose dispensing state;

FIG. 11 shows a partial section view of the device of FIG. 9 in a partially assembled state;

FIGS. 1 and 2 show a drug delivery device in the form of an injection pen. The device has a distal end (left end in FIG.

Figure 1:
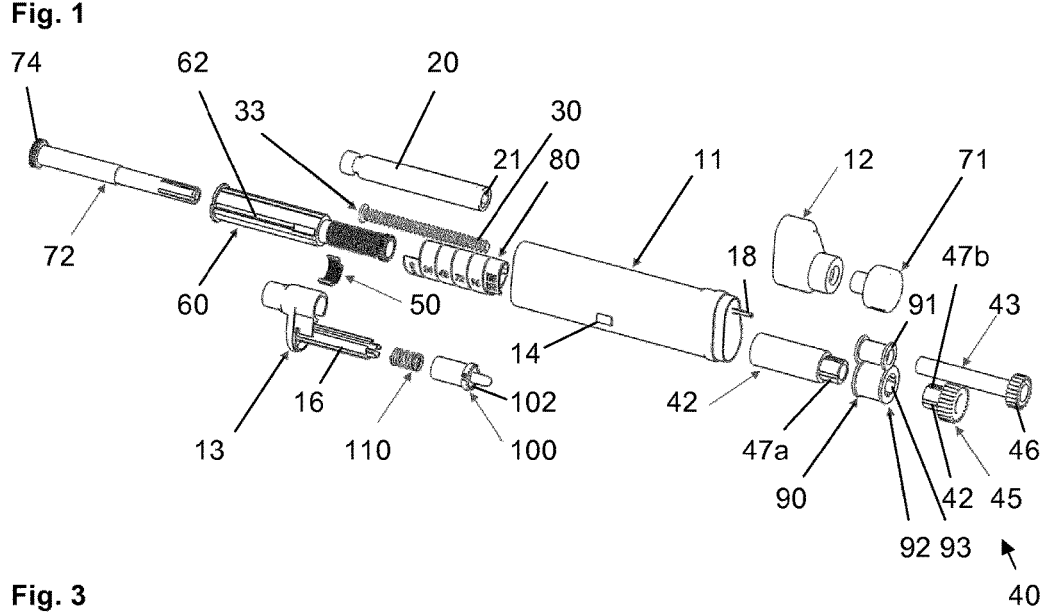
FIG. 1 shows an exploded view of the components of an injection device in accordance with a first embodiment of the present invention.
Figure 2:
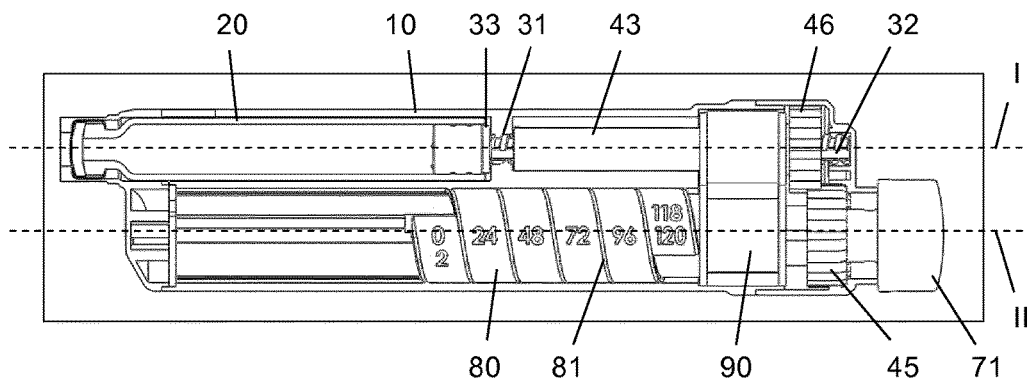
FIG. 2 shows a partial section view of the device of FIG. 1.
Figure 5:
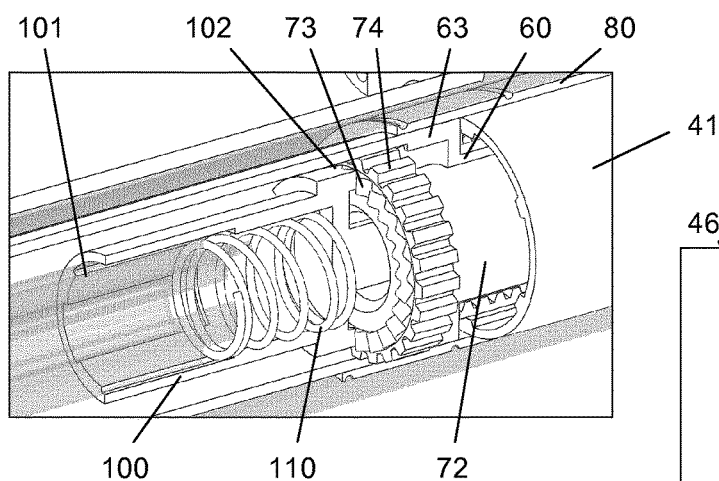
FIG. 5 shows an enlarged view of a detail of the device of FIG. 1.

2) and a proximal end (right end in FIG. 2). The component parts of the drug delivery device are shown in FIG. 1. The drug delivery device comprises a housing 10, a cartridge 20, a lead screw (piston rod) 30, a driver 40, a nut 50, a dial sleeve 60, a dial assembly 70, a number sleeve 80, a power reservoir (motor spring) 90, a clicker 100 and a spring 110. A needle arrangement (not shown) with a needle hub and a needle cover may be provided as additional components, which can be exchanged as explained above.

The housing 10 or body comprises a main housing 11, a proximal housing 12 and a distal housing or cartridge holder 13. The main housing 11 is a generally tubular element with an oblong cross section with the lower side in FIG. 1 being widened compared with the upper side. A window 14 or aperture is provided in the main housing 11. The main housing 11, the proximal housing 12 and the cartridge holder 13 can be plugged or snapped together during assembly to close both open ends of the main housing 11. Further, the housing components may be glued or welded together to form a rigid and permanently attached housing unit. The cartridge holder 13 has a distal aperture in its upper region in FIG. 2, which may have an outer thread or the like for attachment of a needle arrangement. The proximal housing 12 has a proximal aperture in its lower region in FIG. 2. Further, the proximal housing 12 has on its inside near the proximal aperture a ring of teeth 15 (shown in more detail in the embodiment of FIG. 9) which forms part of a clutch with the driver 40. The cartridge holder 13 has on its lower side a splined pin 16 for guiding the clicker 100 and spring 110. The housing 10 provides location for the liquid medication cartridge 20, which is held in the upper part (as seen in FIG. 1) of the main housing 11 and the cartridge holder 13.

The main housing has an inner wall with a threaded section 17 engaging piston rod 30. Further, there is a clicker arm 18 near the proximal end of main housing 11, which arm interacts with the driver 40 during dose dispensing.

The cartridge 20 is a glass ampoule with a movable rubber bung 21 located in its proximal aperture.

The lead screw 30 is an elongate member with an outer thread 31 which is rotationally constrained to the driver 40 via a splined interface. The interface comprises at least one longitudinal groove or track 32 and a corresponding protrusion or spline 44 of the driver 40. When rotated, the lead screw 30 is forced to move axially relative to the driver 40, through its threaded interface 17 with the housing 10. The distal end of the piston rod 30 is provided with a bearing 33, which may abut the cartridge bung 21.

The driver 40 comprises a drive sleeve, which has for manufacturing reasons a drive sleeve lower part 41 and a drive sleeve upper part 42, and a drive tube 43. The drive sleeve lower part 41 and the drive sleeve upper part 42 are rigidly connected to form a unit when in use. The drive tube 43 is arranged on a first longitudinal axis I and the drive sleeve is arranged on a second longitudinal axis II, which is parallel to and spaced from the first axis I.

On the inside of the drive tube 43, splines 44 are provided engaging corresponding grooves 32 of the piston rod 30. The drive tube 43 surrounds the piston rod 30 which is axially displaceable relative to the drive tube 43. As shown in FIGS. 1 to 4, the drive sleeve upper part 42 and the drive tube 43 each have at their proximal end a pinion 45, 46, which mesh such that rotation of the drive sleeve 41, 42, is transmitted to the drive tube 43. The drive sleeve 41, 42, is axially movable along the second axis II between a proximal position (during dose setting and correcting, see FIG. 3) in which pinion 45 further engages teeth 15 of the housing 10, and a distal (dose dispensing position, see FIG. 4) in which the pinion 45 is disengaged from the teeth 15. However, in both axial positions pinions 45, 46 remain in at least partial engagement.

The drive sleeve 41, 42, has on its outer surface splines 47a, 47b for rotationally constraining the drive sleeve to the power reservoir 90. Further, splines 48 are provided on the inner surface of the drive sleeve 41, 42, for rotationally constraining the drive sleeve 41, 42, to nut 50.

The nut 50 is part of a last dose limiter mechanism. The last dose nut 50 is located between the dial sleeve 60 and the drive sleeve 41, 42. It moves along a helical path relative to the dial sleeve 60, via a threaded interface 61, when relative rotation occurs between the dial sleeve 60 and drive sleeve during dialing, i.e. during dose setting or dose correcting. In the embodiments of FIGS. 1 to 11, the nut 50 is a half nut, i.e. a component extending approximately 180° around the second axis II of the device.

The dial sleeve 60 is a tubular element arranged rotatably on the second axis II. A proximal section of the dial sleeve 60 is provided with a thread 61 guiding the nut 50. An adjacent distal section is provided with outer splines 62 for engagement with the number sleeve 80. Further, the dial sleeve 60 has a ring of inner teeth 63 at an intermediate stepped portion for releasably rotationally coupling the dial sleeve 60 to the dial assembly 70. Outer splines 64 are provided at the proximal end for engaging corresponding inner splines of the driver 40 during dose dispensing.

The dial assembly 70 comprises dial grip 71 and a tubular element 72 which is rigidly attached to the dial grip 71. The dial grip 71 and the tubular element 72 are in the present embodiment separate components for manufacturing reasons but may as well be a single component. The dial assembly 70 is arranged on the second axis II and extends through the proximal aperture in the proximal housing part 12. At its distal end, the dial assembly is provided with a ring of detent teeth 73 on its distal face for interaction with clicker 100. Further, splines 74 are provided near the distal end of tubular element 72 engaging splines 63 in the dose setting position. The dial assembly 70 is axially movable along the second axis II between a proximal position (during dose setting and correcting, see FIG. 3) and a distal (dose dispensing position, see FIG. 4). The dial grip 71 abuts the drive sleeve 41, 42, such that axial movement of the dial grip 71 in the distal direction entrains the drive sleeve 41, 42, and axial movement of the drive sleeve 41, 42, in the proximal direction entrains the dial grip 71.

The number sleeve 80 is a tubular element arranged on the second axis II. The outer surface of the number sleeve 80 is provided with a sequence of numbers arranged on a helical path. Further, the number sleeve has on its outer surface a thread 81 engaging a corresponding thread of the main housing 11. At its distal end, the number sleeve 80 is provided with an inwardly directed protrusion 82 for interaction with the clicker 100. Further, there are rotational hard stops on the number sleeve 80 and corresponding elements on the main housing 11 limiting the rotational movement of the number sleeve relative to the housing on its helical path defined by the threaded interface.

The power reservoir comprises a reverse wound flat spiral spring 90, that is a band-like spring, which has a spiral form in its unstressed condition and is wound counter to that unstressed spiral direction for tensioning the spring. A first end of the spring 90 is attached to a first spool 91, which is located on the first longitudinal axis I surrounding drive tube 43. A second end of the spring 90 is attached to a second spool 92, which is located on the second longitudinal axis II and is rotationally constrained to the drive sleeve 41, 42, by splines 47a, 47b and corresponding grooves 93 inside the second spool 92. Spring 90 is fully charged (tensioned) during assembly of the device by winding the spring on spool 92, whereas the spring tends to wind back on spool 91. The power reservoir is dimensioned such that spring 90 is able to drive the piston rod 30 from its retracted position shown in FIGS. 2 to 4 to a position, where the cartridge bung is pushed in its most distal direction. In other words, recharging of the spring 90 is not necessary for emptying cartridge 20.

The clicker 100 is a tubular element positioned axially displaceable but rotationally constrained on splined pin 16 of the cartridge holder 13. As can be seen in FIGS. 8a to 8c, the clicker 100 has grooves 101 on its inner surface for engagement with the splined pin 16. Further, there are detent teeth 102 on the proximal end of clicker 100 mating with teeth 73 of the dial assembly 70. A finger 103, which interacts with protrusion 82 of the number sleeve, is provided near the detent teeth 102.

Figure 3:
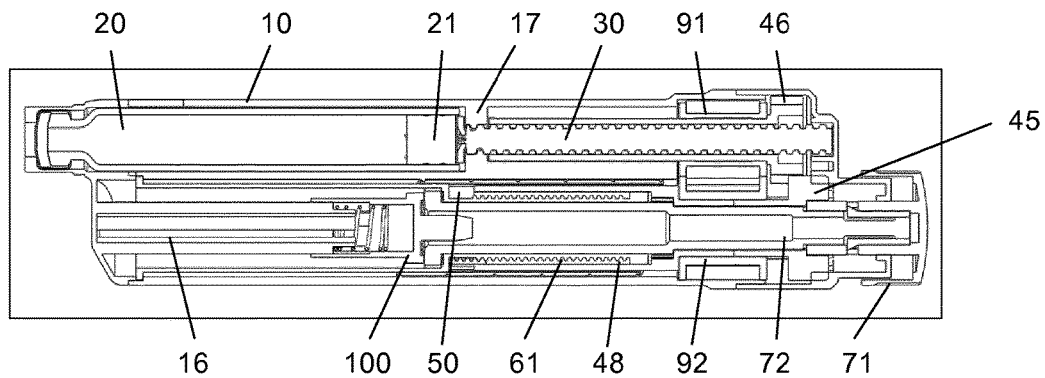
FIG. 3 shows a sectional view of the device of FIG. 1 in the dose setting state.
Figure 4:
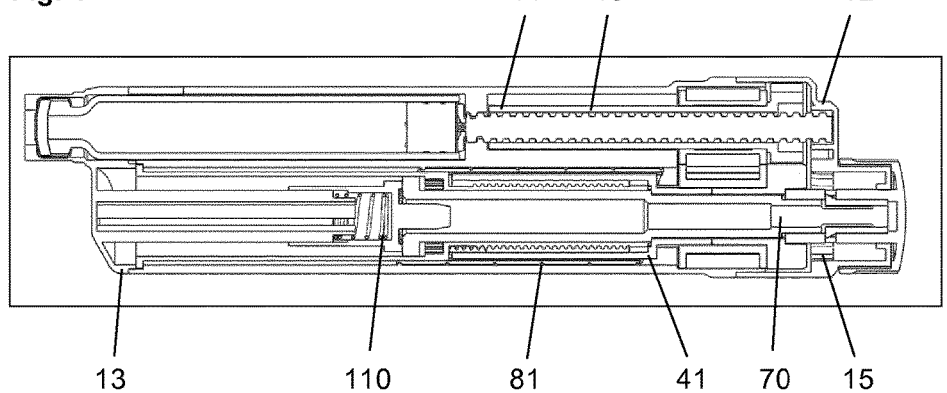
FIG. 4 shows a sectional view of the device of FIG. 1 in the dose dispensing state.

Spring 110 is a compression spring located on splined pin 16 and inside clicker 100 urging clicker 100 in the proximal direction. Due to the contact between the clicker 100 and the dial assembly 70 and due to the contact between the dial assembly 70 and the drive sleeve 41, 42, the spring 110 pushes these components in the proximal direction as shown in FIG. 3, whereas a user may overcome the spring 110 force and push these components in the distal position shown in FIG. 4.

In the following, the functioning of the disposable drug delivery device and its components will be explained in more detail.

Rotation of the dial grip 71 causes the number sleeve 80 to travel between the 0U and 120U stops in the housing 10. There is an axial detent toothed interface between the clicker 100 and tubular element of the dial assembly 70 (which are forced together by the spring 110) which generates the detented dose positions and user feedback. The drive sleeve 41, 42 is rotationally restrained during dialing via a splined interface to the housing 10.

The key interfaces during dialing are: the dial sleeve 60 is splined to the dial grip 71, the number sleeve 80 is splined to the dial sleeve 60, the number sleeve 80 is threaded to the housing 10, the clicker 100 is splined to the cartridge holder 13 10, the drive sleeve 41, 42 is splined to the splined pin 16, the nut 50 is threaded to the dial sleeve 60, and the nut 50 is splined to the drive sleeve 41, 42.

The zero and maximum dose stops are generated by abutments between the number sleeve 80 and housing 10. User input torque, applied to the dial grip 71, is reacted via the dial sleeve 60 and number sleeve 80 back to the housing 10 when the abutments are engaged.

The nut 50 advances towards a rotational abutment at the proximal end of the dial sleeve 60 whilst there is relative rotation between the dial sleeve 60 and drive sleeve 41, 42. When the abutment is reached, dial torque is reacted through the dial grip 71, dial sleeve 60, nut 50 and drive sleeve 41, 42 back to the splined interface with the housing 10.

To dispense a dose, the dial grip 71 is pressed by the user. It then disengages from the dial sleeve 60, and is rotationally constrained by the clicker 100 detent teeth engagement (between the tubular element 72 of the dial assembly 70 and the clicker 100). Axial force applied by the user is reacted by the spring 110, and by a direct abutment between the dial grip 71 and the housing 10. As the dial grip 71 is rotationally decoupled from the mechanism during dispensing, the user is unable to input abuse torques to the dispensing mechanism or adjust the dose.

The drive sleeve 41, 42 is moved axially so that it first engages spline features 64 with the dial sleeve 60 then disengages from its splined interface 45, 15, with the housing 10. The spring 90 then causes the drive sleeve 41, 42 to rotate. Via the geared interface between the drive sleeve 41, 42 and the drive tube 43, the drive tube 43 is rotated which then drives the piston rod 30 through the housing 10 into the bung 21. The drive sleeve 41, 42 causes the number sleeve 80 to rotate back towards the 0U position, via the dial sleeve 60.

The key interfaces during dispensing are: the drive sleeve 41, 42 is axially constrained to the dial grip 71 and displaced towards distal end of the device, the dial grip 71 disengages from the dial sleeve 60, the drive sleeve 41, 42 engages with splines on the dial sleeve 60, and the drive sleeve 41, 42 disengages from the housing 10.

Dispensing of a dose continues until the number sleeve 80 reaches its 0U abutment with the housing 10, or the user releases the dial grip 71. When the 0U abutment engages, torque from the spring 90 is reacted via the dial sleeve 60 and number sleeve 80 into the housing 10. If the user releases the dial grip, the action of the spring 110 acts to re-engage the splined interface 15, 45, between the drive sleeve 41, 42 and housing 10.

Feedback during dose setting is provided by an interaction between the tubular element of the dial assembly 70 and the clicker 100. The clicker 100 is splined to the cartridge holder 13 splined pin 16, and the spring 110 forces the clicker 100 into axial engagement with the tubular element of the dial assembly 70. Detent teeth 73, 102 provide an axial detent toothed interface between the components and the clicker 100 shuttles axially as the dial grip 71 is rotated, providing detented positions for the dial grip. This is shown in more detail in FIG. 5, where splines 74 of tubular element 72 are shown disengaged from the inner ring of splines 63 of the dial sleeve 60, i.e. the device is in its dose dispensing position. Further, teeth 73 and teeth 102 are shown.

Figure 6:
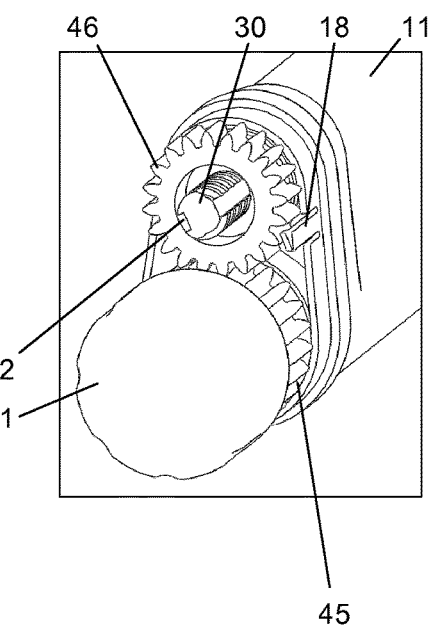
FIG. 6 shows an enlarged view of a detail of the device of FIG. 1.
Figure 7:
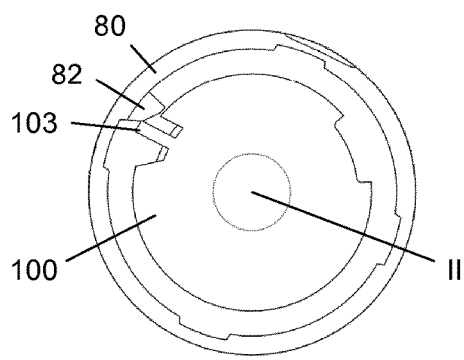
FIG. 7 shows an enlarged view of a detail of the device of FIG. 1.

During dose dispense, tactile and audible feedback is created by the interaction of the drive tube 43 and the housing 10. As shown in FIG. 6, there is a compliant clicker arm 18 integrated into the main housing 11 which is displaced by rotation of the gear teeth 46 on the drive tube 43. The clicker arm 18 contacts the surface of the proximal housing 12 as the gear teeth 46 pass over the clicker arm 18, generating feedback for each dose unit dispensed.

At the completion of the delivery of a dose, as the number sleeve 80 returns to its 0U position, additional audible feedback is created by the interaction of the number sleeve 80 and the clicker 100. As shown in FIGS. 8a to 8c, this interaction is dependent on the axial position of the clicker 100, and only occurs during dispense, when the clicker 100 is in its distal position, when the dial grip 71 is depressed by the user. By utilising the axial position of the dial grip to create this interaction, the end of dose feature does not need to be overhauled by the user during dialing of a dose (see FIG. 8c).

In this embodiment, a radial finger 103 extends from the clicker 100, and a protrusion in the form of a ramped boss 82 is added to the inner surface of the number sleeve 80, such that the boss on the number sleeve 80 deflects the radial finger 103 as the number sleeve 80 rotates back from the 1U position (shown in FIG. 8a) to the 0U position (shown in FIG. 8b). As the number sleeve 80 returns to the 0U position, the radial finger 103 is released and springs back to its at rest state creating audible feedback to the user. As the clicker 100 is in direct contact with the dial assembly, tactile feedback will also be provided, as the dial grip will be being held in its depressed state by the user.

It is possible to incorporate a mechanism that allows the user to control the speed of dispense by the degree of travel that they input to the dial grip 71. The second embodiment shows in FIGS. 9 to 10*b* a multi-plate clutch system 120 integrated into the device acting between the housing 10 and the drive sleeve 41, 42. This system comprises first clutch plates 121, which are splined to the upper drive sleeve 42, and second clutch plates 122 which are splined to a cage 123. The cage 123 has outer splines 124 engaging with corresponding grooves in the proximal housing 12 to rotationally constrain cage 123. A clutch spring 125 is interposed between the proximal housing 12 and the clutch plates 121, 122 within the cage 123.

Multiple clutch plates increase the torque capacity of the clutch for a given clutch spring force. For the embodiment shown in FIG. 9, force applied to the clutch pack 121, 122 from the clutch spring 125 (FIG. 10*a*) reduces as the dial grip 71 is depressed, because the upper drive sleeve 42 is pushed by the dial grip 71 together with the cage 123 in the distal direction and away from the proximal housing 12 (FIG. 10*b*).

In this embodiment, the overall dial grip 71 travel is increased to e.g. 5 mm, 2.5 mm for mechanism disengagement to commence dispense and 2.5 mm for user variable speed control. As the force applied by the clutch spring 125 reduces as the dial grip 71 is depressed, the frictional torque applied to the drive sleeve 41, 42 by the clutch pack 121, 122 also reduces, and the value of the frictional torque is dependent on the axial position of the dial grip 71. The torque available from the spring 90 must overcome the frictional torque of the clutch pack, which reduces the torque applied to the mechanism to dispense a dose. The speed of dispense therefore increases as the user continues to depress the dial grip 71 between the disengagement position and the full travel position. The force required to depress the dial grip 71 increases with its travel due to the combined actions of the spring 110 and clutch spring 125, with spring 110 increasing the resistance despite the weaker spring 125 reducing the resistance.

The facility for removing the need for a user to prime the device when first used is also provided. This involves removing the variable distance (dependant on component and cartridge tolerances) between the cartridge bung 21 and the bearing 33 during manufacture such that the bearing 33 is in contact with, or applying a light load to, the bung 21 when assembled.

This "prime elimination" is achieved using the following method: Rotation of the drive tube 43, independently from the drive sleeve 41, 42, advances the piston rod 30 for prime elimination. Therefore, prior to the proximal housing 12 being fitted, the drive tube 43 is displaced towards the proximal end of the device, so that it no longer engages with the drive sleeve 41, 42 gear teeth 45 (see FIG. 11). The drive tube 43 is then rotated to advance the piston rod 30 and hence its bearing 33 towards the cartridge bung 21. Contact with the bung 21 can either be sensed using measurement of the torque required to rotate the drive tube or by measurement of the axial position of the piston rod 30 relative to the thread 17 in the housing 10. The point at which the piston rod 30 moves to the opposite sides of its threaded engagement with the housing 10 indicates contact with the bung 21.

Figure 12:
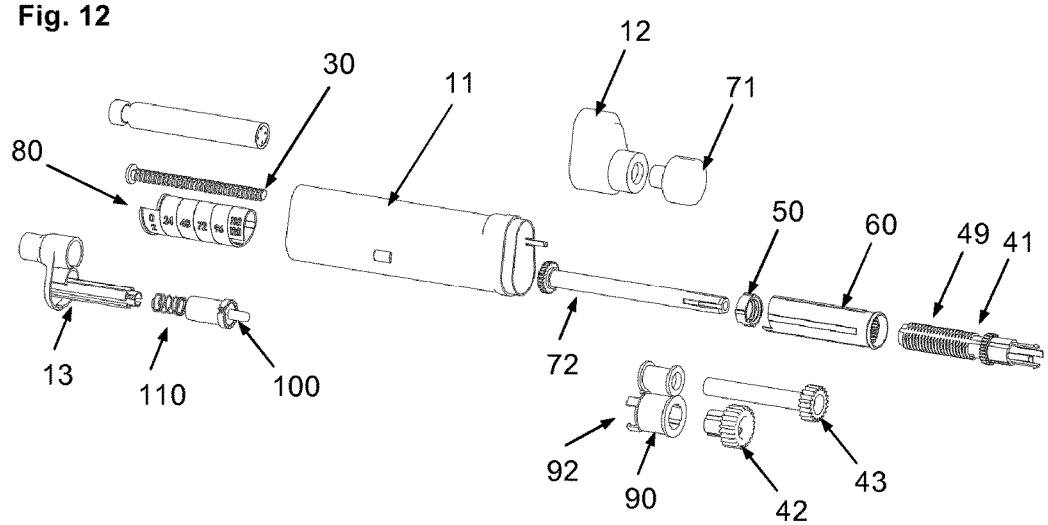
FIG. 12 shows an exploded view of the components of an injection device in accordance with a third embodiment of the present invention.
Figure 13:
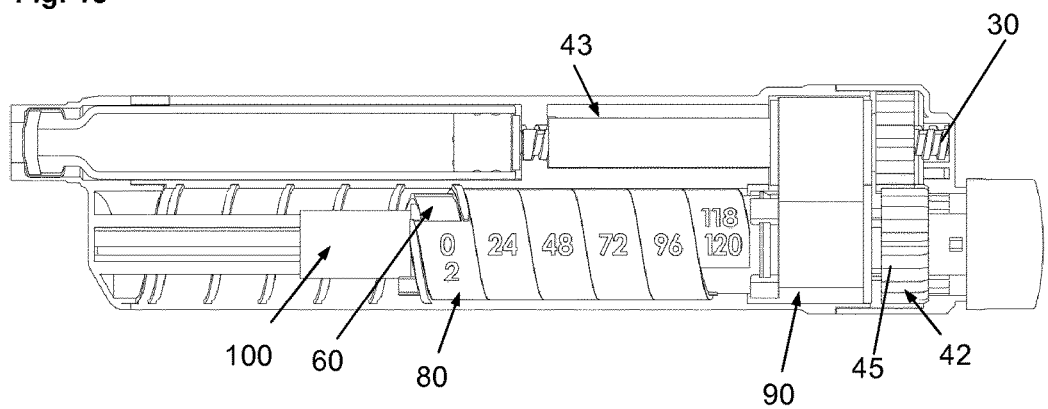
FIG. 13 shows a view of the device of FIG. 11.
Figure 14:
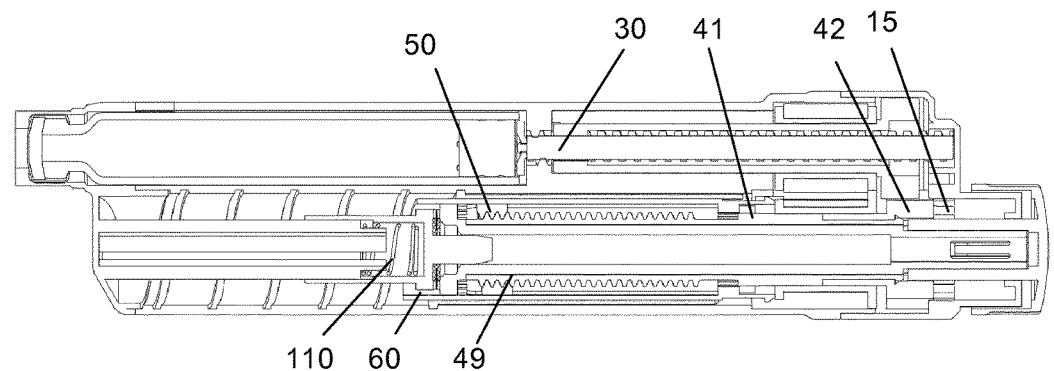
FIG. 14 shows a sectional view of the device of FIG. 11 in the dose setting state.

A third, alternative embodiment is shown in FIGS. 12 to 14. Where appropriate, similar components are given the same reference numerals as in the first embodiment. The design and function of this device is in general very similar to that of the first embodiment. Further, this device is suitable for the speed control of the second embodiment and allows prime elimination as described above.

The main changes with respect to the first embodiment relate to the drive sleeve 41, 42, the dial sleeve 60 and to the nut 50 of the last dose mechanism. Again, the drive sleeve comprises for manufacturing reasons two component parts 41, 42 which are snapped together to behave as a single component. However, the drive sleeve 41, 42 has a prolonged distal part 41 with a threaded section 49. On the other hand, dial sleeve 60 is shorter without the threaded section 61 of the first embodiment. The nut 50, which is a full nut in this embodiment, runs with its inner thread on this threaded section 49. Further, the nut 50 has a splined outer surface which is axially displaceably guided in grooves on the inner surface of dial sleeve 60.

Again, as a user sets a dose, the dial sleeve 60 rotates together with the dial assembly 70, whereas the drive sleeve 41, 42 is coupled to the housing 10 via teeth 15, 45. Thus, nut 50 travels on the threaded section 49. During dose dispensing, the drive sleeve 41, 42, is decoupled from the housing and rotates together with the dial sleeve 60, such that the nut 50 maintains its relative position on the drive sleeve.

The invention claimed is:

1. An injection device comprising
   a housing containing a cartridge containing a medicament and a movable bung, wherein the housing comprises an inner thread,
   a piston rod for moving the bung during dose dispensing, the piston rod comprising an outer thread engaging the inner thread of the housing and a bearing facing the bung and positioned at a distal end of the piston rod, wherein, in an unused delivery state of the device, the bearing abuts the bung, and
   a driver coupled to the piston rod for driving the piston rod during dose dispensing.

2. The injection device of claim 1, wherein the driver comprises a drive tube directly coupled to the piston rod and a drive sleeve coupled to a power reservoir to drive the drive tube in a distal direction.

3. The injection device of claim 2, wherein the power reservoir comprises a pre-loaded spring.

4. The injection device of claim 2, wherein the drive tube and the drive sleeve are rotationally coupled to each other such that rotation of the drive tube in a first direction causes rotation of the drive sleeve in a second direction.

5. The injection device of claim 4, wherein the drive tube and the drive sleeve are coupled to each other by meshing gears such that the drive tube and the drive sleeve rotate in opposite directions.

6. The injection device of claim 1, further comprising a dose setting member, wherein the piston rod defines a first longitudinal axis and the dose setting member defines a second longitudinal axis parallel to and spaced apart from the first longitudinal axis.

7. The injection device of claim 6, wherein:
   the driver comprises a drive tube directly coupled to the piston rod and a drive sleeve coupled to a power reservoir to drive the drive tube in a distal direction,
   the drive tube is rotatable about the first longitudinal axis, and
   the drive sleeve is rotatable about the second longitudinal axis.

8. The injection device of claim 6, wherein a portion of at least one of the dose setting member and the driver is axially displaceable along the second longitudinal axis between a dose setting position and a dose dispensing position,
- wherein, in the dose setting position, the dose setting member is rotatable relative to the housing and relative to the driver, and
- wherein, in the dose dispensing position, the driver is rotatable relative to the housing.

9. The injection device of claim 6, further comprising:
- a first spool located on the first longitudinal axis and a second spool located on the second longitudinal axis, one of the first spool and the second spool being coupled to the driver; and
- a reverse wound flat spiral spring having a first end attached to the first spool and a second end attached to the second spool located on the second longitudinal axis.

10. The injection device of claim 6, wherein:
- the dose setting member comprises a dial assembly and a dial sleeve,
- the dial assembly and the dial sleeve are rotatable about the second longitudinal axis, and
- the dial assembly is decoupled from the driver during dose setting and is coupled to the driver during dose dispensing.

11. The injection device of claim 6, further comprising a number sleeve in threaded engagement with the housing and in splined engagement with the dose setting member.

12. The injection device of claim 6, comprising:
- a limiter mechanism positioned with the housing to engage the dose setting member to define a maximum settable dose and a minimum settable dose, and
- a last dose protection mechanism positioned within the housing for preventing the dose setting member from being set to an excess dose exceeding an amount of remaining medicament in the cartridge.

13. The injection device of claim 6, wherein the dose setting member comprises a release button axially displaceable along a longitudinal axis of the injection device, wherein displacement of the release button in a first direction along the longitudinal axis increases a friction force on the driver, and displacement of the release button in a second direction along the longitudinal axis decreases the friction force on the driver.

14. The injection device of claim 1, further comprising a release clutch preventing rotation of the driver relative to the housing during dose setting and allowing rotation of the driver relative to the housing during dose dispensing.

15. The injection device of claim 1, wherein the piston rod is rotationally constrained to a portion of the driver and is axially displaceable relative to the portion of the driver.

16. The injection device of claim 1, further comprising a clicker that produces an audible and/or tactile first feedback during dose setting and/or during dose dispensing.

17. The injection device of claim 16, wherein the clicker comprises a protrusion and a flexible member, the protrusion and the flexible member being positioned such that the protrusion contacts the flexible member to produce the audible and/or tactile feedback.

18. The injection device of claim 16, wherein the clicker is a first clicker, and the injection device further comprises a second clicker that produces an audible and/or tactile second feedback, distinct from the first feedback, during dose dispensing when the device reaches its minimum dose position.

19. The injection device of claim 1, wherein a length of the injection device along a longitudinal axis of the injection device before dose setting is equal to a length of the injection device along the longitudinal axis of the injection device after dose setting.

* * * * *